(12) United States Patent
Storr et al.

(10) Patent No.: US 8,142,844 B2
(45) Date of Patent: Mar. 27, 2012

(54) SEPARATING MATERIAL

(75) Inventors: Markus Storr, Filderstadt (DE); Egbert Müller, Darmstadt (DE); Wolfgang Freudemann, Hechingen (DE)

(73) Assignee: Gambro Lundia AB, Lund (SE)

( * ) Notice: Subject to any disclaimer, the term of this patent is extended or adjusted under 35 U.S.C. 154(b) by 695 days.

(21) Appl. No.: 10/572,703

(22) PCT Filed: Aug. 30, 2004

(86) PCT No.: PCT/EP2004/051953
§ 371 (c)(1),
(2), (4) Date: Mar. 17, 2006

(87) PCT Pub. No.: WO2005/026224
PCT Pub. Date: Mar. 24, 2005

(65) Prior Publication Data
US 2006/0264355 A1    Nov. 23, 2006

Related U.S. Application Data

(60) Provisional application No. 60/521,404, filed on Apr. 20, 2004.

(30) Foreign Application Priority Data

Sep. 17, 2003  (EP) .................................... 03020986

(51) Int. Cl.
*B05D 3/12* (2006.01)
*B01D 39/14* (2006.01)
(52) U.S. Cl. .................. 427/245; 427/244; 210/500.37; 210/500.27; 210/500.23; 210/645
(58) Field of Classification Search ............ 210/500.23, 210/500.35, 500.37, 500.38, 500.27, 645; 427/244, 245
See application file for complete search history.

(56) References Cited

U.S. PATENT DOCUMENTS 4,097,420 A    6/1978   Mikes et al.
(Continued)

FOREIGN PATENT DOCUMENTS

EP    0 052 156    5/1982
(Continued)

OTHER PUBLICATIONS

Drumheller et al., Surface Immobilization of Adhesion Ligands for Investigations of Cell-Substrate Interactions, 2000, CRC Press, The Biomedical Engineering Handbook, 2nd Edition, pp. 1-14.*

(Continued)

*Primary Examiner* — Tony G Soohoo
*Assistant Examiner* — David C Mellon
(74) *Attorney, Agent, or Firm* — Barnes & Thornburg LLP

(57) ABSTRACT

The present invention provides a separating material producable by a) providing a solid substrate, having amino-functional groups coupled to the substrate surface, b) covalently coupling of the amino-functional groups with a thermally labile radical initiator, c) contacting the substrate surface with a solution of polymerizable monomers under conditions, where thermally initiated graft copolymerization of the monomers takes place, to form a structure of adjacent functional polymer chains on the surface of the substrate. The present invention further provides a method for the production of a separating material by a) providing a solid substrate, having aminofunctional groups coupled to the substrate surface, b) covalently coupling of the aminofunctional groups with a thermally labile radical initiator, c) contacting the substrate surface with a solution of polymerizable monomers under conditions, where thermally initiated graft copolymerization of the monomers takes place, to form a structure of adjacent functional polymer chains on the surface of the substrate.

34 Claims, 2 Drawing Sheets

Experimental set-up for dynamic Endotoxin adsorption of grafted membranes from citrate-anticoagulated human blood (Example 10)

- Blood from healthy donor, V=70ml, T=37°
- LPS: E. coli, 3 EU/ml
- 270 min recirculation
- Membrane module: A=200 $cm^2$, n(fiber)=144, $l_{eff}$=12 cm fibers
- $\gamma$ = 500$s^{-1}$ ($Q_B$=8ml/min), $Q_F$=1ml/min, TMP<50mm$_{Hg}$

U.S. PATENT DOCUMENTS

| | | | |
|---|---|---|---|
| 4,618,533 A * | 10/1986 | Steuck | 428/315.7 |
| 4,668,399 A * | 5/1987 | Duggins | 210/637 |
| 4,784,495 A | 11/1988 | Jonsson et al. | |
| 5,037,656 A * | 8/1991 | Pitt et al. | 424/443 |
| 5,152,901 A * | 10/1992 | Hodgdon | 210/654 |
| 5,215,692 A | 6/1993 | Horl et al. | |
| 5,344,560 A | 9/1994 | Sugo et al. | |
| 5,453,186 A | 9/1995 | Muller et al. | |
| 5,476,509 A | 12/1995 | Keogh et al. | |
| 5,532,311 A * | 7/1996 | Sirvio et al. | 525/54.2 |
| 5,556,708 A | 9/1996 | Horl et al. | |
| 5,866,673 A | 2/1999 | Muller et al. | |
| 5,967,714 A | 10/1999 | Ottersbach et al. | |
| 6,096,800 A | 8/2000 | Ottersbach et al. | |
| 6,361,768 B1 * | 3/2002 | Galleguillos et al. | 424/70.12 |
| 6,774,102 B1 | 8/2004 | Bell et al. | |

FOREIGN PATENT DOCUMENTS

| | | |
|---|---|---|
| EP | 0 109 531 | 5/1984 |
| EP | 0 278 100 B1 | 8/1988 |
| WO | WO 91/03506 | 3/1991 |
| WO | WO-91/13098 | 9/1991 |
| WO | WO 00/12575 | 3/2000 |
| WO | WO-01/19878 A1 | 3/2001 |
| WO | WO-01/23413 A1 | 4/2001 |
| WO | WO-01/92359 A1 | 12/2001 |
| WO | WO 01/94032 A1 | 12/2001 |

OTHER PUBLICATIONS

Duner, Kristina I., "A new kinetic single-stage *Limulus amoebocyte* lysate method for the detection of endotoxin in water and plasma," *Journal of Biochemical and Biophysical Methods*, 26 (1993) 131-142.

* cited by examiner

Figure 1: Endotoxin (LPS) concentration before and after columns (example 9)

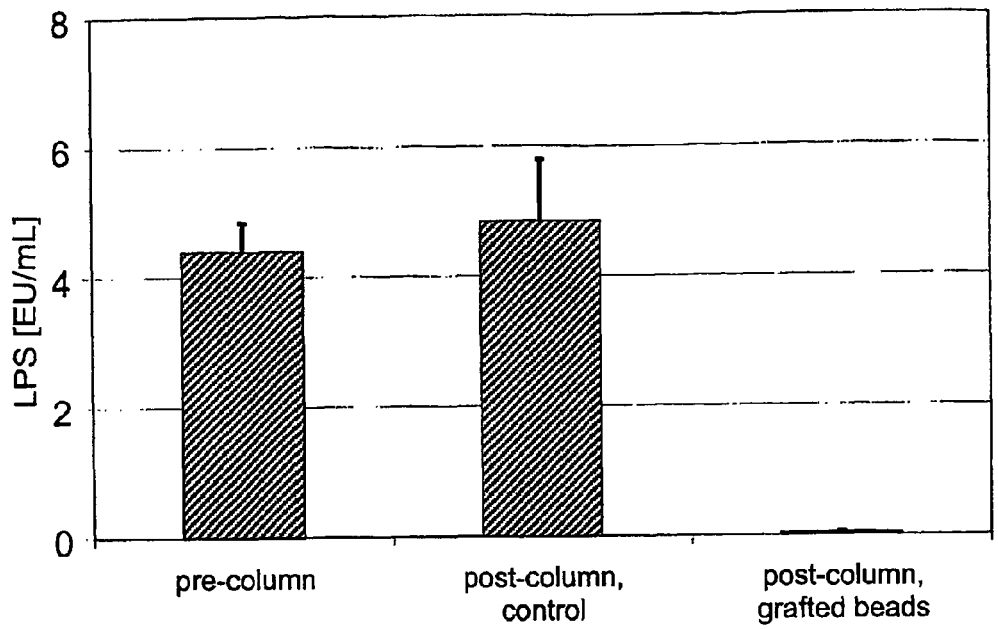

Figure 2: Experimental set-up for dynamic Endotoxin adsorption of grafted membranes from citrate-anticoagulated human blood (Example 10)

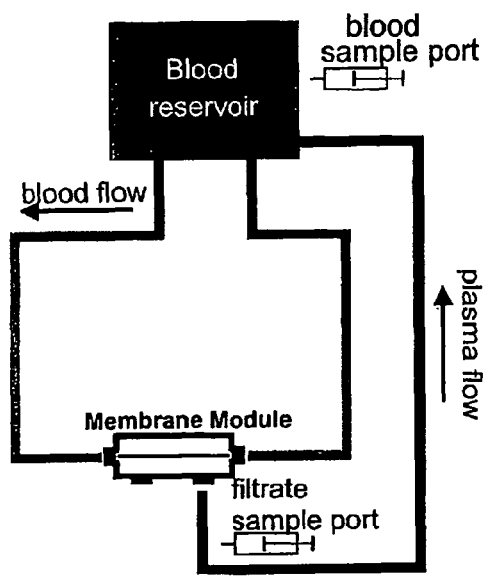

- Blood from healthy donor, V=70ml, T=37°
- LPS: E. coli, 3 EU/ml
- 270 min recirculation
- Membrane module: A=200 $cm^2$, n(fiber)=144, $l_{eff}$=12 cm fibers
- $\gamma$ = 500$s^{-1}$ ($Q_B$=8ml/min), $Q_F$=1ml/min, TMP<50mm$_{Hg}$ Figure 3: Endotoxin reduction in filtrated plasma fraction (example 10)
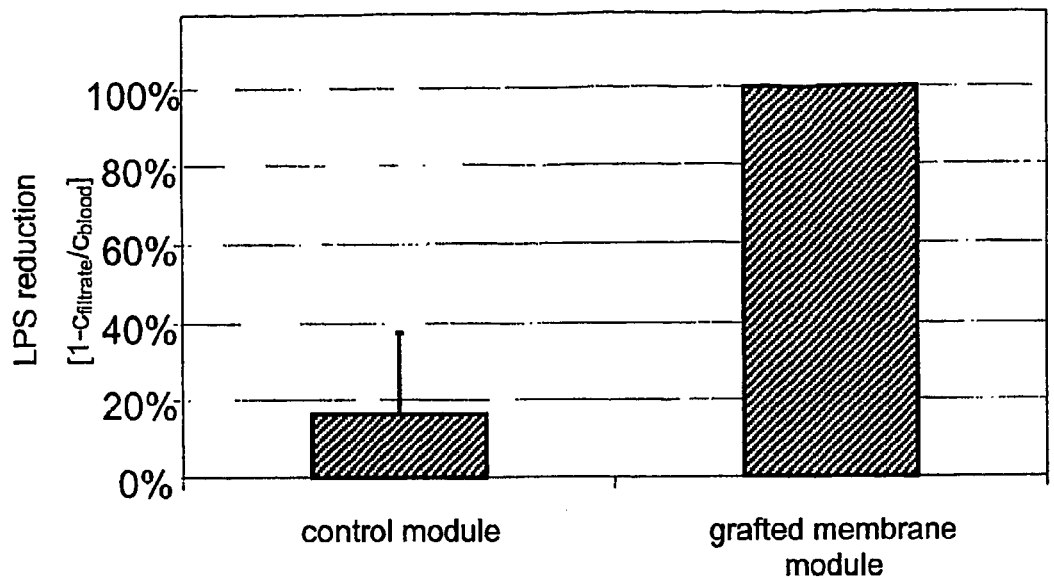
Figure 4: Endotoxin concentration in blood reservoir (example 10)
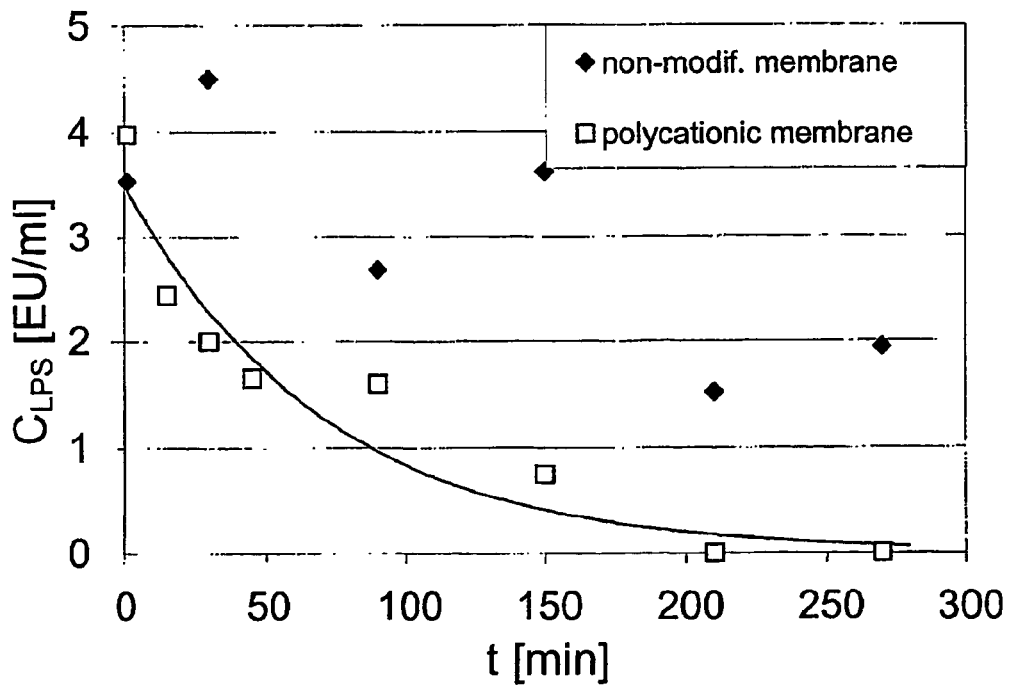

SEPARATING MATERIAL

CROSS REFERENCE TO RELATED APPLICATIONS

This application is an national phase application based on PCT/EP2004/051953, filed Aug. 30, 2004, the content of which is incorporated herein by reference, and claims the benefit of U.S. Provisional Application No. 60/521,404, filed Apr. 20, 2004, the content of which is incorporated herein by reference, and claims the right to priority based on European Application No. 03020986.0, filed Sep. 17, 2003, the content of which is incorporated herein by reference.

BACKGROUND OF THE INVENTION

The present invention relates to a separating material, a novel method for producing the same, and the use of the separating material in several separating applications.

By separating material it is meant a material that is useful as an adsorption material and/or as a dialysis material and/or as a filtration material for the separation of substances, having specific chemical or physical properties, or substances, being recognized by specific recognition compounds, from a fluid, especially a liquid. Separating materials in the sense of the present invention are particularly useful in the separation or depletion, respectively, of undesired substances from liquids, e. g. the adsorptive separation of toxins from blood plasma.

Separating materials for adsorptive separation applications generally comprise a solid phase substrate material or matrix material, respectively, which carries on its surface active sites for the more or less specific adsorption of compounds having particular properties, e. g. positive or negative charges, specific chemical structures or functional groups etc. The solid phase substrate material may often be a porous or non-porous polymer having functional surface groups or chains of a graft copolymer being functionalized and being formed by graft polymerization of monomers onto the surface of the polymeric matrix material.

The U.S. Pat. No. 5,556,708 describes a method for the production of an adsorption material by graft polymerization of a nitrogen-containing polymer with an ethylenically unsaturated monomer in an aqueous environment in the presence of two reactants, said two reactants consisting of carbon tetrachloride and a reducing agent, selected from sodium dithionite, rongalite, hydrazine, and ascorbic acid. According to the description and the examples of U.S. Pat. No. 5,556,708, sodium dithionite seems to be the only one reducing agent that had been tested. Also, even though it is claimed that the nitrogen-containing polymer may be selected from polyamides, polysulfonamides, polyurethanes, and polymers having primary and secondary amine groups in a side chain, only a polyamide membrane, particularly a nylon 6,6 membrane, had been tested in the examples as the nitrogen-containing polymer. U.S. Pat. No. 5,556,708 leaves unclear whether and how the method may work with a nitrogen-containing polymer having primary and secondary amine groups. It is known that amides form radicals with the reducing agents used according to U.S. Pat. No. 5,556,708, but there is no mechanistical explanation how the graft polymerization should work with primary and secondary amines.

One major disadvantage of the method of U.S. Pat. No. 5,556,708 is the prescribed use of an organic reactant, especially of carbon tetrachloride in the graft polymerization process. Even if the produced material is thoroughly cleaned after the production process, there will still be amounts of carbon tetrachloride remaining in the porous polymeric structure. The toxicity of carbon tetrachloride thus makes the produced adsorption material inappropriate for medical applications, as e. g. the adsorption of toxins from blood or in hemodialysis. On the other hand, the more or less complete removal of carbon tetrachloride from the adsorption material of U.S. Pat. No. 5,556,708 by exhaustive rinsing or washing of the material would cause enormous costs and would make the material commercially unattractive.

Summarizing, disadvantages of prior art separating materials include the following: the substrate materials are not biocompatible or blood compatible, thus the materials are not useful for medical applications; the reactions to produce such separating materials require organic solvents which are toxic or biohazardous, thus the materials are not useful for medical applications; the reaction conditions to produce such separating materials are often harsh in a way that the preparation methods are restricted to reactants which withstand such conditions; and the reactions to produce such separating materials, if UV activation is used, do not provide for a uniform functionalization over the entire surface of a porous polymeric matrix.

SUMMARY OF THE INVENTION

It is an object of the present invention to provide a separation material and a method for producing the same, whereby the above-mentioned disadvantages of the prior art are overcome. It is another object of the present invention to provide a separation material that is useful for medical applications.

Accordingly, the present invention provides a separating material producable by:
  a) providing a solid substrate, having amino-functional groups coupled to the substrate surface,
  b) covalently coupling of the amino-functional groups with a thermally labile radical initiator,
  c) contacting the substrate surface with a solution of polymerizable monomers under conditions, where thermally initiated graft copolymerization of the monomers takes place, to form a structure of adjacent functional polymer chains on the surface of the substrate.

In another aspect the present invention provides a method for the production of a separating material by:
  a) providing a solid substrate, having amino-functional groups coupled to the substrate surface,
  b) covalently coupling of the amino-functional groups with a thermally labile radical initiator,
  c) contacting the substrate surface with a solution of polymerizable monomers under conditions, where thermally initiated graft copolymerization of the monomers takes place, to form a structure of adjacent functional polymer chains on the surface of the substrate.

Preferably, the separating material of the present invention is produced by the afore-mentioned method. One advantage of the present invention is that the method of producing the separating material of the present invention does not require an organic solvent, such as carbon tetrachloride, which is difficult to remove from the final product, and which may be toxic or at least harmful to a patient, when the separating material is used in medical applications and extracorporeally contacted to any liquid or body fluid, which is (re-)introduced into the patient's body.

Another advantage of the present invention lies in the covalently coupling of the radical initiator to the amino-functional groups on the solid substrate. Thereby, the occurrence of homopolymerization in the reaction solution is avoided or at least minimized. The radical initiator, which is bound to the solid substrate, forms radicals upon temperature increase, and part of the radical initiator structure becomes part of the polymer chains, which are formed from the solid substrate surface. The polymer chains of the present invention develop from the surface of the substrate without the formation of undesired cross-linkages between the chains, thus the process of the present invention is considered to provide a very "clean" chemistry.

Another advantage of the present invention is based on the use of thermally labile radical initiators, which can be chosen to ensure mild reaction conditions and to avoid additional reactants which may react with the substrate or the monomers in an undesired manner. The temperatures to initiate radical formation of useful radical initiators typically lie within the range of 50° C. to 120° C., preferably in the range of 70° C. to 100° C. A useful temperature range of the polymerization reaction is from the 10 hour half life temperature of the radical initiator to about 20 to 25 degrees above that 10 hour half life temperature. By adjusting the reaction temperature it is further possible to very precisely control the polymerization reaction, e. g. onset of the reaction, reaction speed, degree of polymerization etc.

In a preferred embodiment of the separating material of the present invention, the solid substrate is a porous polymeric material. The porosity of the substrate material provides a large surface area for the contact between the separating material and the fluid.

An advantageous use of the separating material is the medical application in the extracorporeal treatment of human or animal blood or other body fluids, e. g. hemodialysis, filtration, and/or removal of undesired substances from the blood by adsorption of such substances to the separating material. Usually, in such applications the blood of a patient is extracorporeally separated into the blood cells and the blood plasma (or blood serum), the latter containing most of the substances to be removed by the treatment. In another preferred embodiment of the invention the porous polymeric material has a pore size that is sufficiently large to allow passage of blood plasma, or blood serum through the substrate material. This allows the blood plasma or blood serum to get in contact with the entire surface area within the pores of the separating material. In another embodiment the porous polymeric material has a pore size that is sufficiently large to allow passage of blood plasma, or blood serum through the substrate material, whereby the pore size is sufficiently small to avoid passage of the blood cells. This allows the use of the separation material, if it is in the form of a membrane or a hollow fibre membrane, to separate the blood cells from the blood plasma by passing whole blood onto or by the membrane. Thereby, the blood cells are retained on one side of the membrane, whereas blood plasma can pass through the pores of the membrane to the opposite side of the membrane. Thus, blood cells are filtered from the blood plasma. While the blood plasma is passing the separating material membrane, it is contacted within the pores of the material to the active surface of the material. Thereby, the separating material depletes the blood plasma from undesired substances by adsorption. Afterwards, the depleted or purified blood plasma may be recombined with the blood cells and for example be reinjected into the patient's circulation, or it may be stored for later use.

The separating material of the present invention may be provided in any form, but preferably is in the form of a membrane, a hollow fibre membrane, a particle bed, a fibre mat, or beads. Most preferred it is in the form of a hollow fibre membrane, as it is for example well known from hemodialysis applications. Multiple hollow fibre membranes can by known procedures be potted into tubes, and the tubes being fitted with ports in a known manner, to provide separating units, which preferably are in the form of cartridges useful to be inserted into dialysis apparatuses. If the separating material of the present invention is provided in the form of beads, such beads can for example be packed into columns for the passage of the fluid to be treated, e. g. blood plasma.

In another preferred embodiment the separating material of the present invention is made of a biocompatible material, to avoid any hazardous effects on a treated body liquid of a patient or on the patient itself, if the treated liquid is reinfused into the patient.

Preferred materials useful for the preparation of the separating material of the present invention are selected from the group, consisting of polyacrylates, polystyrene, polyethylene oxide, cellulose, cellulose derivatives, polyethersulfone (PES), polypropylene (PP), polysulfone (PSU), polymethylmethacrylate (PMMA), polycarbonate (PC), polyacrylonitrile (PAN), polyamide (PA), polytetrafluorethylene (PTFE), cellulose acetate (CA), regenerated cellulose, and blends or copolymers of the foregoing, or blends or copolymers with hydrophilizing polymers, preferably with polyvinylpyrrolidone (PVP) or polyethyleneoxide (PEO).

Preferably, the amino-functional groups on the solid substrate for the production of the separating material of the invention are primary amino groups, even though secondary amino groups may also be useful. Primary amino groups provide for a higher reactivity.

In a highly preferred embodiment of the present invention, the thermally labile radical initiator, as the starting material before coupling to the amine groups on the solid substrate, comprises at least one, preferably two carboxylic groups. In the reaction of coupling of the radical initiator to the amine group of the substrate, the carboxylic groups are preferably activated by a water soluble carbodiimide, for example 1-ethyl-3-(3-dimethylaminopropyl)-carbodiimide (EDAC) which forms active o-acylurea intermediates. After initial activation, the carboxyl groups will react with e. g. N-hydroxysuccinimide (NHS) to form an active ester, which couples with the primary amino groups on the surface of the substrate.

Useful thermally labile radical initiators include compounds which decompose to give free radicals on thermal activation. Preferably, the thermally labile radical initiator being selected among azo compounds or peroxides. Most preferred radical initiators are 4,4'-azobis-(4-cyanovaleric acid) or 2,2'-azobis-[N-(2-carboxyethyl)-2-methylpropionamidine.

The monomers useful to form the polymer chains from the substrate surface by graft polymerization are selected from compounds having a polymerizable double bond. Preferred monomers can be divided into three groups: (1) monomers providing positive or negative charges, (2) monomers for binding affinity ligands, and (3) inert hemocompatible monomers.

Preferred monomers of the first group (1) are selected from N,N-Dimethylaminoethyl acrylamide, N,N-Diethylaminoethyl acrylamide, N,N-Dimethylaminopropyl acrylamide (DMPA), N,N-Dimethylaminopropyl methacrylamide, N,N-Dimethylaminoethyl methacrylate, N,N-Dieethylaminoethyl methacrylate, N,N-Dimethylaminoethyl acrylate, N-Morpholinoethyl acrylate, N-Morpholinoethyl methacrylate, 1-Vinylimidazole, Trimethylammoniumethyl acrylamide, Trimethylammoniumpropyl methacrylamide, and Trimethylammoniumethyl methacrylate. The most preferred monomer of this group is Dimethylaminopropyl acrylamide (DMPA).

Preferred monomers of the second group (2) are selected from Glycidyl acrylate, Glycidyl methacrylate, Vinyl glycidyl ether, and Vinyl glycidyl urethane. The most preferred monomer of this group is Glycidyl methacrylate.

Preferred monomers of the third group (3) are selected from 2-Hydroxyethyl methacrylate, 2-Hydroxypropyl methacrylate, Hydroxymethyl methacrylate, N-Vinylpyrrolidone, 2-Vinyl pyridine, 4-Vinyl pyridine, and N-Vinyl-2-methylimidazole. The most preferred monomer of this group is 2-Hydroxyethyl methacrylate.

The polymerization reaction can comprise one single type of monomer of the above-mentioned, or it can be carried out using two or more different types of monomers of the same or different of the above groups.

Highly preferred polymerizable monomers are selected from compounds of the following formula:

$$H_2C=C(R^1)-C(O)-X-R^2-N(R^3)_2,$$

wherein $R^1$=hydrogen, methyl or ethyl group; $R^2$=C1-C6-alkyl or aryl group; $R^3$=methyl or ethyl group; and X=NH or O.

BRIEF DESCRIPTION OF THE DRAWINGS

The invention will now be described and further illustrated by way of preferred reaction schemes, examples and the accompanying figures.

FIG. 1 illustrates data of the measurement of the endotoxin concentrations according to example 9, described below.

FIG. 2 illustrates the experimental set-up for dynamic endotoxin adsorption of grafted membranes from citrate-co-agulated human blood according to example 10, described below.

FIG. 3 illustrates data of the measurement of the endotoxin concentrations in filtrates according to example 10, described below.

FIG. 4 illustrates data of the measurement of the endotoxin concentrations in the blood reservoir according to example 10, described below.

DETAILED DESCRIPTION OF THE INVENTION

Preferred Reaktion Schemes

1. For illustration purposes, by way of example the separating material of the present invention can be produced, e. g. using N,N-dimethylaminopropylacrylamide as the polymerizable monomer. This monomer provides a basic group which is positively charged at physiologic pH. Therefore, the produced separating material is effective to adsorb negatively charged substances by charge interaction, e. g. bacterial toxins such as endotoxins from gram-negative bacteria, lipoteichoic acid from gram-positive bacteria or bacterial DNA. Using the produced separating material, a number of tests have been carried out with respect to endotoxin removal from plasma or blood (see below). The production of the thus produced separating material is illustrated in reaction scheme 1 below.

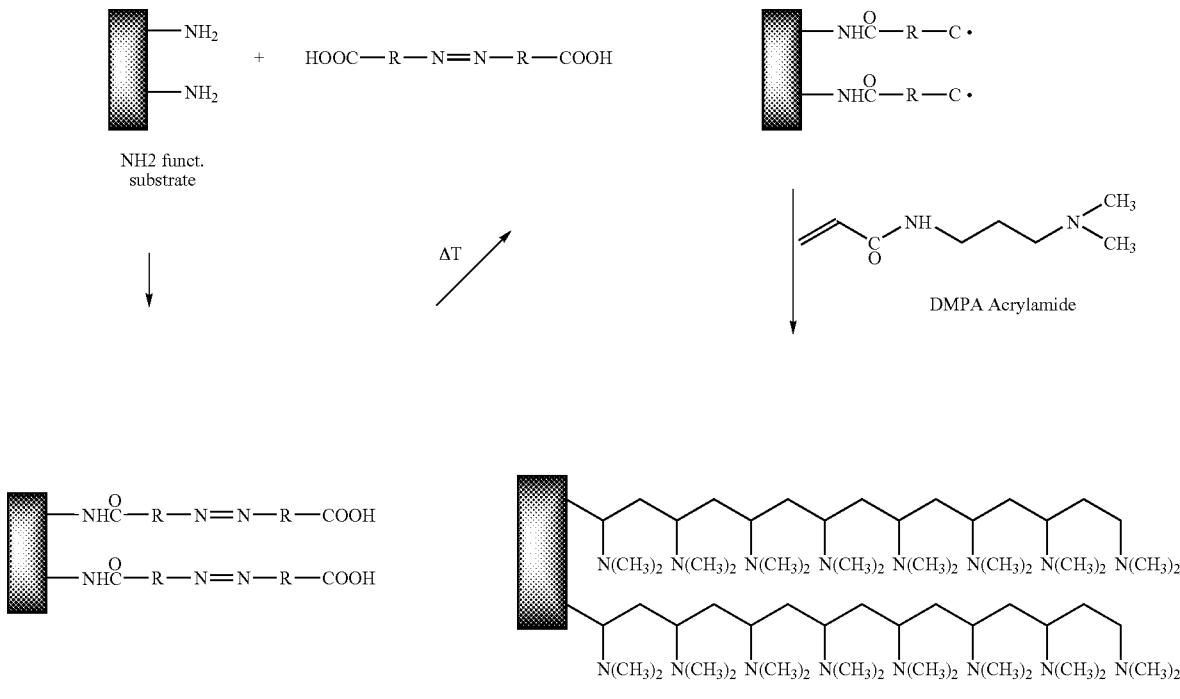

In the first reaction step the polymerisation initiator is covalently coupled to the support. Therefore, the amino-group containing supports are reacted with activated esters, e.g. carbodiimide or anhydride activated carboxylic groups of the initiator. Thereby the polymerization initiator is bound to the activated sites. Suitable polymerization initiators are compounds which decompose to give free radicals at thermal activation, e.g. azo compounds or peroxides, and which further carry reactive substituents, e.g. carboxylic groups. Particularly preferred initiators are azo carboxyl compounds, such as 4,4'-azobis(4-cyanovaleric acid) or 2,2'-azobis[N-(2-carboxyethyl)-2-methylpropionamidine]. The carboxyl groups are preferably activated by the water soluble carbodiimide 1-ethyl-3-(3-dimethylaminopropyl)-carbodiimide (EDAC) which forms active o-acylurea intermediates. After initial activation by EDAC, the carboxyl groups will react with N-hydroxysuccinimide (NHS) to form an active ester, which couples with the primary amino groups on the surface of the substrate. When using 4,4'-azobis(4-cyanovaleric acid) as initiator the reaction can be carried out in organic solutions such as DMF, DMSO or toluene. The reaction can also be carried out in aqueous solution at a pH>12, which is preferable for medical applications.

Concentration ranges of compounds for modification of 1-10 9 substrate (membane or beads):
20-200 ml solvent
0.1-10 g 4,4'-Azobis(4-cyanovaleric acid)
0.2-20 g EDA
0.2-20 g NHS Reaction temperature: 0-30° C., most preferably room temperature for simplicity reasons Reaction time: 1 to a several hours In the second reaction step the initiator immobilized surface is contacted with a solution of N,N-dimethylaminopropyl acrylamide. The reaction can be carried out in degased water in an inert atmosphere. The temperature is chosen above the 10 hour half life temperature of the initiator. The grafting reaction typically uses 1 to 20 g N,N-dimethylaminopropyl acrylamide dissolved in from 10 to 300 ml water. The reaction is typically carried out at from 70 to 95° C., and typically takes from 30 min to several hours.

Other monomers suitable for introducing positive charges are, inter alia, N,N-dimethylaminoethyl acrylamide, N,N-diethylaminoethyl acrylamide, N,N-dimethylaminoethyl methacrylate N,N-dimethylaminoethyl acrylamide, N,N-dimethylaminopropyl methacrylamide and trimethylammoniumethyl acrylamide.

2. In another illustrating example the separating material of the present invention can be produced, e. g. using glycidyl methacrylate as the polymerizable monomer. This type of monomer is used for subsequent binding of affinity ligands such as proteins, peptides, antibodies or other biological molecules. The epoxide groups can also be reacted with amino compounds, such as diethylamine, triethylamine or arginine, to give positively charged adsorbents. Other monomers which comprise both a polymerizable double bond and an oxirane ring are for example glycidyl acrylate, vinyl glycidyl ether and vinyl glycidyl urethane. The production of the thus produced separating material is illustrated in reaction scheme 2 below.

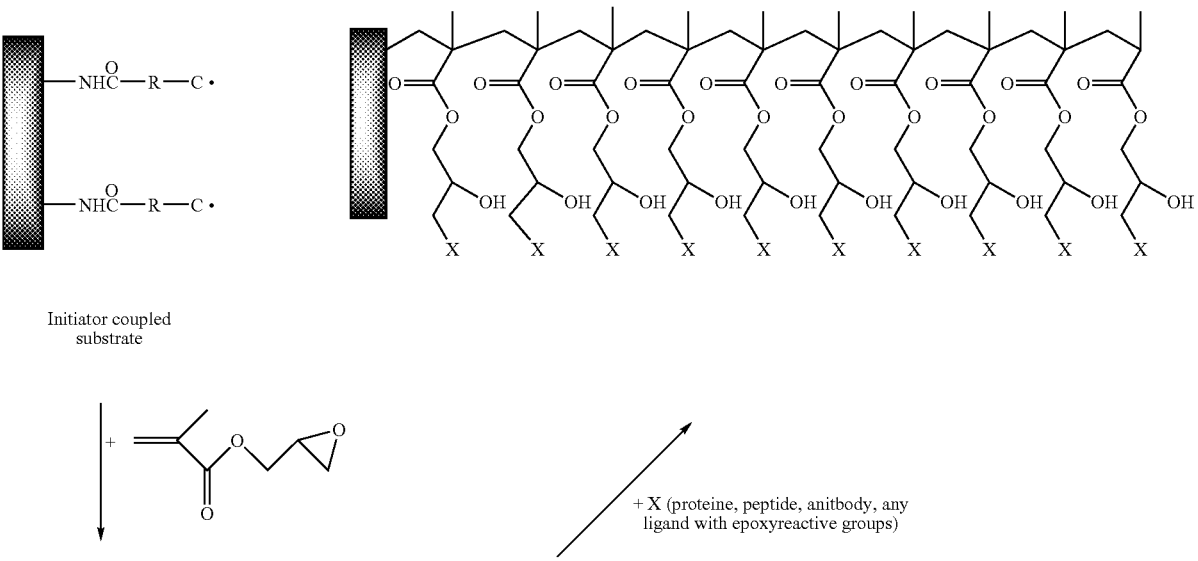

-continued

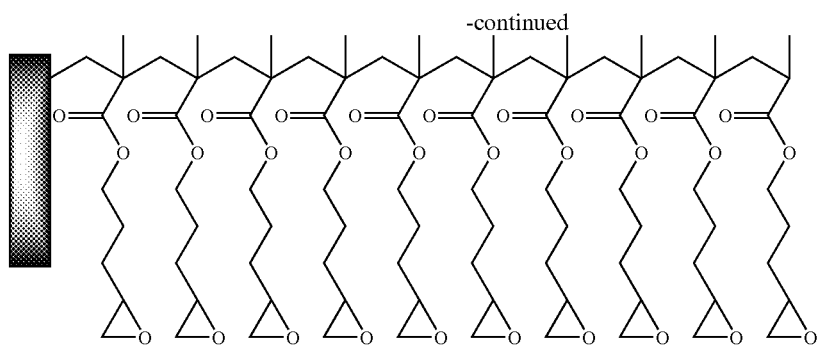

In the first reaction step coupling of polymerisation initiator is performed as described above in connection with reaction scheme 1. In the second reaction step the surface is contacted again with a solution of the monomer at elevated temperature in an inert atmosphere.

Reaction Components:
1-10 g Substrate (membrane or beads)
1-20 g Glycidyl methacrylate
10-400 ml solvents (water, ethanol, ethanol, toluene, DMF, DMSO)

3. In another illustrating example the separating material of the present invention can be produced using a mixture of a functional monomer and an inert monomer as the polymerizable monomers. The monomers can be used alone, as also illustrated above, or in a mixture with inert monomers, e.g. vinyl pyrrolidone, hydroxymethyl methacrylamide or hydroxyethyl acrylate in order to increase the hydrophilicity of the polymer or/and to improve the biocompatibility of the materials. The production of the thus produced separating material is illustrated in reaction scheme 3 below.

EXAMPLE 1

Coupling of 4,4'-azobis(4-cyanovaleric Acid) onto Macroporous Acrylic Beads 200 g oxirane acrylic resin beads (e.g. Toyo Pearl HW70EC, Tosoh Corp.) having an average epoxy group content of 4.0 mmol/g are aminated with 150 ml conc. ammonia solution (32 wt %) for 3 hours at 40° C. After washing with distilled water, 45 g beads are resuspended in 400 ml DMF and 10 g 4,4'-azobis(4-cyanovaleric acid). 15 g EDAC and 15 g NHS are added. The batch is agitated for 12 hours at room temperature and afterwards rinsed with water.

EXAMPLE 2

Coupling of 4,4'-azobis(4-cyanovaleric Acid) onto Microporous Hollow Fiber Membranes A bundle of polyethersulfon/polyvinylpyrrolidone hollow fibre membranes (144 fibres, 25 cm long, inner diameter 260

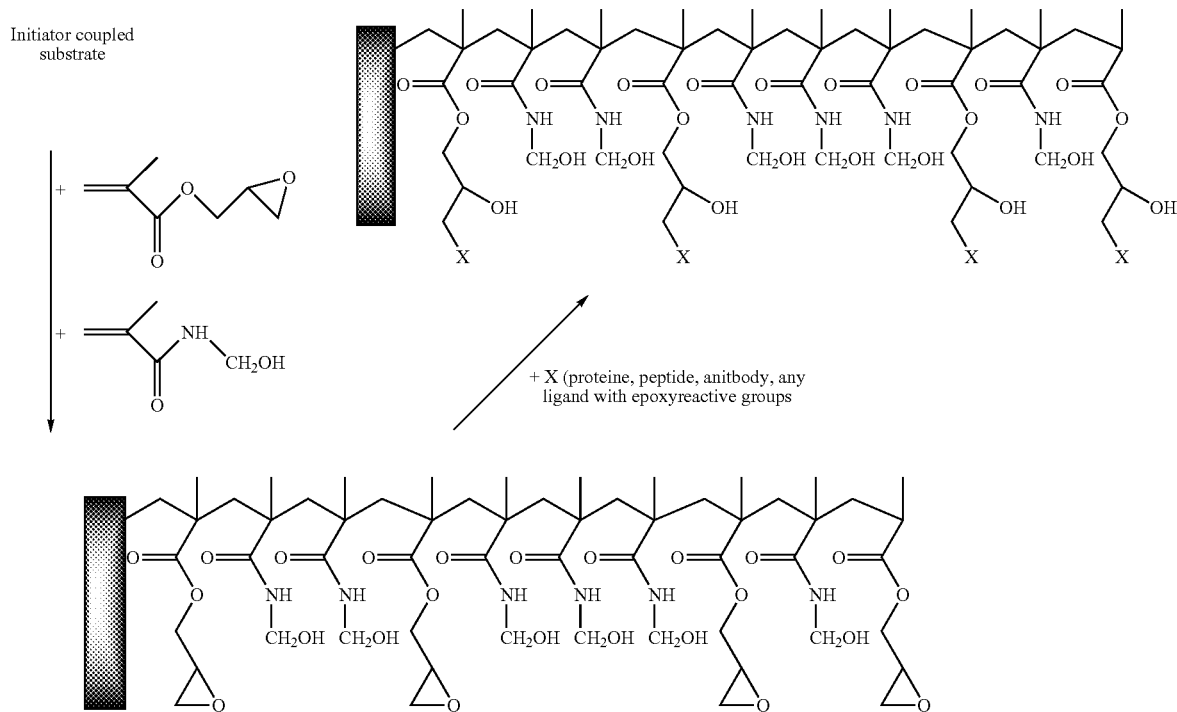

μm, outer diameter 340 μm, mean pore diameter 0.3 μm, functionalised with 1.5 μmol/g primary amino groups by plasma treatment as described in Swedish patent application 020107-8) is incubated with 0.6 g 4,4'-azobis(4-cyanovaleric acid) and 0.85 g NHS in 45 ml 0.1 M NaOH. Then 0.85 g EDAC dissolved in 5 ml 0.1 M NaOH is added and agitated for 12 h at room temperature. Afterwards the excess reagents are removed by washing repeatedly with water.

EXAMPLE 3

Graft Polymerisation of Beads with N,N-dimethylaminopropylacrylamide 15 g beads derivatized as in Example 1 are reacted in a reaction solution of 0.45 g N,N-dimethylaminopropylacrylamide in 75 ml degassed water in a three-necked flask. The reaction is performed with gentle stirring at 75° C. for 3 hours in an atmosphere of nitrogen. The derivatized beads are then rinsed as follows: 1 l hot water, 50 ml 1 M NaOH, 50 ml 1 M HCl, 0.5 l water, 0.5 l PBS buffer (pH=7.4), 0.5 l 1 M NaCl solution and 0.5 l water.

EXAMPLE 4

Graft Polymerisation of Beads with glycidyl methacrylate 20 g beads derivatized as in Example 1 are reacted in a reaction solution of 8.0 g glycidyl methacrylate in 120 ml toluene in a three-necked flask. The reaction is performed with gentle stirring at 75° C. for 3 hours in an atmosphere of nitrogen (reflux condenser). The derivatized beads are then thoroughly rinsed as described in example 3 and dried overnight at 40° C. in a vacuum drying oven. The degree of grafting is found to be 125%.

EXAMPLE 5

Graft Polymerisation of Microporous Membranes with N,N-dimethylaminopropyl acrylamide A bundle of membranes derivatized as in Example 2 is reacted in a reaction solution of 2,5 g N,N-dimethylaminopropyl acrylamide in 40 ml degassed water in a three-necked flask. The reaction is performed with gentle stirring at 75° C. for 12 hours in an atmosphere of nitrogen. The derivatized membranes are then thoroughly rinsed as described in example 3. To prepare a membrane device the bundle was dried and potted at each end of a 10 mm-diameter poly(carbonate) tube fitted with two ports in the shell.

EXAMPLE 6

Graft Polymerisation of Microporous Membranes with glycidyl methacrylate

A bundle of membranes derivatized as in Example 2 is reacted in a reaction solution of 1.0 g glycidyl methacrylate in 40 ml Isopropanol water in a three-necked flask. The reaction is performed with gentle stirring at 75° C. for 3 hours in an atmosphere of nitrogen. The derivatized membranes are then thoroughly rinsed as described in example 3 and reacted with 2.0 g oligo arginine in 40 g water, which has been synthesized as described in WO0123413.

EXAMPLE 7

Graft Polymerisation of Microporous Membranes with a Mixture of glycidyl methacrylate and hydroxymethyl methacrylamide A bundle of membranes derivatized as in Example 2 is reacted in a reaction solution of 0.6 g glycidyl methacrylate and 2.4 g hydroxymethyl methacrylamide in 40 ml degassed water in a three-necked flask. The reaction is performed with gentle stirring at 75° C. for 3 hours in an atmosphere of nitrogen. The derivatized membranes are then thoroughly rinsed as described in example 3 and dried overnight at 40° C. in a vacuum drying oven. The degree of grafting is found to be 122.5%.

EXAMPLE 8

Determination of the Grafting Yield and Protein Binding Capacity

The dynamic protein binding capacity of the adsorbents produced in examples 3, 5, and 6 was determined by establishing the breakthrough curves of the membrane modules or fixed bed columns filled with the grafted beads in dead-end filtration mode and single-pass perfusion mode, respectively. Thereby a solution of bovine serum albumin (1 g/l in 20 mM Tris pH 8.0) is pumped through the modules or columns at a perfusion rate of 1 ml/min. The effluent is monitored by a flow-through UV-detector cell at 280 nm. The results are shown in the following table 1.

TABLE 1

| Adsorbent | Degree of grafting [%] | Dynamic BSA binding capacity [mg/g substrate] |
|---|---|---|
| Example 3 | 117 | 180 |
| Example 5 | 104 | 166 |
| Example 6 | 108 | 99 |

EXAMPLE 9

Dynamic Endotoxin Adsorption of Grafted Beads from Citrate-Anticoagulated Human Blood 4 g beads grafted with N,N-dimethylaminopropylacrylamide, as described in example 3, are packed into a poly (carbonate) column. A column with 4 g acrylate beads not reacted with any ligand is used as control. To eliminate potential contamination the column is perfused with 100 ml 30% ethanol (0.1 M NaOH, 8.8 g/l NaCl), followed by 200 ml Ringer/ACD solution and 100 ml pyrogen-free 0.9% saline. Endotoxin (LPS from *E. coli,* 055B.5) is added to freshly donated citrate anticoagulated human blood at a concentration of 10 EU/ml. 150 ml blood prepared in this manner is then passed through the columns at a flow rate of 1.3 ml/min. Aliquots of 1 ml were taken before and after the test columns and assayed for LPS content using chromogenic Limulus Amebocyte Lysate (LAL) test (Charles River Endosafe, Inc.) as described by K. Duner, (1993) *Journal of Biochem. and Biophys. Method* 26:131-142. The results are shown in FIG. 1.

EXAMPLE 10

Dynamic Endotoxin Adsorption of Grafted Membranes from Citrate-Anticoagulated Human Blood Membrane modules prepared as in Example 5 waeresterilized with steam and rinsed in filtration mode with 200 ml pyrogen-free 0.9% saline. Then 90 ml Citrate-anticoagulatede fresh human whole blood spiked with 3 EU/ml Endotoxin (LPS from *E. coli*, 055B.5) was perfused from a blood reservoir through the module under recirculating conditions, as it is shown in FIG. 2. The blood flow rate was 8 ml/min and plasma is filtrated at a flow rate of 1 ml/min through the membrane of the membrane module. To avoid a dilution effect the first 20 ml blood were withdrawn after perfusion. After 30 min, 90 min, 150 min, 210 min, and 270 min aliquots of 1 ml were taken from the filtrate and from the blood reservoir, as illustrated in FIG. 2 (filtrate sample port; blood sample port), and assayed for LPS content using the LAL test described in example 9. A membrane module with membranes not modified with ligands is used in a control experiment. As shown in FIG. 3 the spiked endotoxin was completely removed from the plasma fraction filtrated through the membrane. As shown in FIG. 4, the treatment resulted in a 100% reduction of endotoxin in the blood pool after 210 minutes of perfusion.

The invention claimed is:

1. A method for producing a separating material comprising the steps of:
   a) providing a solid substrate having a substrate surface, wherein primary or secondary amines are coupled to the substrate surface; and
   b) forming a graft polymer on the substrate by a process consisting essentially of the reaction steps of:
      i) covalently coupling the primary or secondary amines with a thermally labile radical initiator and, subsequently,
      ii) contacting the substrate surface with a solution of one or more polymerizable monomers, wherein thermally initiated graft copolymerization of the monomers forms a structure comprising adjacent functional polymer chains on the substrate surface.

2. The method of claim 1, wherein the solid substrate is a porous polymeric material having a pore size sufficiently large to allow passage of blood, blood plasma, or blood serum through the solid substrate.

3. The method of claim 1, wherein the solid substrate is selected from the group consisting of: a membrane, a particle bed, a fibre mat, and beads.

4. The method of claim 1, wherein the solid substrate comprises a biocompatible material.

5. The method of claim 1, wherein the solid substrate comprises a material selected from the group consisting of polyacrylates, polystyrene, polyethylene oxide, cellulose, cellulose derivatives, polyethersulfone (PES), polypropylene (PP), polysulfone (PSU), polymethylmethacrylate (PMMA), polycarbonate (PC), polyacrylonitrile (PAN), polyamide (PA), polytetrafluorethylene (PTFE), cellulose acetate (CA), regenerated cellulose, and blends or copolymers of the foregoing, or blends or copolymers with hydrophilizing polymers.

6. The method of claim 1, wherein the amino-functional groups are primary amino groups.

7. The method of claim 1, wherein the thermally labile radical initiator which is covalently coupled comprises at least one carboxylic group.

8. The method of claim 1, wherein the thermally labile radical initiator which is covalently coupled comprises compounds which decompose to give free radicals upon thermal activation selected from the group consisting of azo compounds and peroxides.

9. The method of claim 1, wherein the thermally labile radical initiator which is covalently coupled is 4,4'-azobis-(4-cyanovaleric acid) or 2,2'-azobis-[N-(2-carboxyethyl)-2-methylpropionamide].

10. The method of claim 1, wherein the one or more polymerizable monomers are selected from compounds having a polymerizable double bond.

11. The method of claim 1, wherein the one or more polymerizable monomers are selected from the group consisting of:
acrylic acid, methacrylic acid, vinyl compounds, derivatives of acrylic acid, methacrylic acid and vinyl compounds, N,N-Dimethylaminoethyl acrylamide, N,N-Diethylaminoethyl acrylamide, N,N-Dimethylaminopropyl acrylamide (DMPA), N,N-Dimethylaminopropyl methacrylamide, N,N-Dimethylaminoethyl methacrylate, N,N-Diethylaminoethyl methacrylate, N,N-Dimethylaminoethyl acrylate, N-Morpholinoethyl acrylate, N-Morpholinoethyl methacrylate, 1-Vinylimidazole, Trimethylammoniumethyl acrylamide, Trimethylammoniumpropyl methacrylamide, Trimethylammoniumethyl methacrylate, Glycidyl acrylate, Glycidyl methacrylate, Vinyl glycidyl ether, Vinyl glycidyl urethane, 2-Hydroxyethyl methacrylate, 2-Hydroxypropyl methacrylate, Hydroxymethyl methacrylate, N-Vinylpyrrolidone, 2-Vinyl pyridine, 4-Vinyl pyridine, and N-Vinyl-2-methylimidazole.

12. The method of claim 1, wherein the one or more polymerizable monomers comprise Dimethylaminopropyl acrylamide (DMPA).

13. The method of claim 1, wherein the one or more polymerizable monomers are selected from compounds of the following formula:

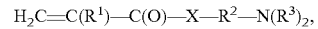

$$H_2C=C(R^1)-C(O)-X-R^2-N(R^3)_2,$$

wherein $R^1$ is hydrogen, methyl or ethyl group; $R^2$ is a $C_1$-$C_6$-alkyl or aryl group; $R^3$ is a methyl or ethyl group; and X is NH or O.

14. The method of claim 3, wherein the solid substrate is a membrane, said membrane comprising a hollow fibre.

15. The method of claim 5, wherein the solid substrate comprises blends or copolymers of said materials.

16. The method of claim 15, wherein the blends or copolymers of said materials further comprise hydrophilizing polymers.

17. The method of claim 16, wherein the hydrophilizing polymer comprises polyvinylpyrollidone (PVP), or polyethyleneoxide (PEO).

18. A method for producing a separating material comprising the step of:
   contacting the substrate surface of a solid substrate having a substrate surface, wherein primary or secondary amines are coupled to the substrate surface and a thermally labile radical initiator is covalently coupled to the primary or secondary amines,
   with a solution of one or more polymerizable monomers, wherein thermally initiated graft copolymerization of the monomers forms a structure including adjacent functional polymer chains on the substrate surface.

19. The method of claim 18, wherein the solid substrate is a porous polymeric material having a pore size sufficiently large to allow passage of blood, blood plasma, or blood serum through the solid substrate.

20. The method of claim 15, wherein the solid substrate is selected from the group consisting of: a membrane, a particle bed, a fibre mat, and beads.

21. The method of claim 20, wherein the solid substrate is a membrane, said membrane comprising a hollow fibre.

22. The method of claim 18, wherein the solid substrate comprises a biocompatible material.

23. The method of claim 18, wherein the solid substrate comprises a material selected from the group consisting of polyacrylates, polystyrene, polyethylene oxide, cellulose, cellulose derivatives, polyethersulfone (PES), polypropylene (PP), polysulfone (PSU), polymethylmethacrylate (PMMA), polycarbonate (PC), polyacrylonitrile (PAN), polyamide (PA), polytetrafluorethylene (PTFE), cellulose acetate (CA), regenerated cellulose, and blends or copolymers of the foregoing, or blends or copolymers with hydrophilizing polymers.

24. The method of claim 23, wherein the solid substrate comprises blends or copolymers of said materials.

25. The method of claim 24, wherein the blends or copolymers of said materials further comprise hydrophilizing polymers.

26. The method of claim 25, wherein the hydrophilizing polymer comprises polyvinylpyrrolidone (PVP), or polyethyleneoxide (PEO).

27. The method of claim 18, wherein the amino-functional groups are primary amino groups.

28. The method of claim 18, wherein the thermally labile radical initiator which is covalently coupled comprises at least one carboxylic group.

29. The method of claim 18, wherein the thermally labile radical initiator which is covalently coupled comprises compounds which decompose to give free radicals upon thermal activation selected from the group consisting of azo compounds and peroxides.

30. The method of claim 18, wherein the thermally labile radical initiator which is covalently coupled is 4,4'-azobis-(4-cyanovaleric acid) or 2,2'-azobis-[N-(2-carboxyethyl)-2-methylpropionamide].

31. The method of claim 18, wherein the one or more polymerizable monomers are selected from compounds having a polymerizable double bond.

32. The method of claim 18, wherein the one or more polymerizable monomers are selected from the group consisting of:

acrylic acid, methacrylic acid, vinyl compounds, derivatives of acrylic acid, methacrylic acid and vinyl compounds, N,N-Dimethylaminoethyl acrylamide, N,N-Diethylaminoethyl acrylamide, N,N-Dimethylaminopropyl acrylamide (DMPA), N,N-Dimethylaminopropyl methacrylamide, N,N-Dimethylaminoethyl methacrylate, N,N-Diethylaminoethyl methacrylate, N,N-Dimethylaminoethyl acrylate, N-Morpholinoethyl acrylate, N-Morpholinoethyl methacrylate, 1-Vinylimidazole, Trimethylammoniumethyl acrylamide, Trimethylammoniumpropyl methacrylamide, Trimethylammoniumethyl methacrylate, Glycidyl acrylate, Glycidyl methacrylate, Vinyl glycidyl ether, Vinyl glycidyl urethane, 2-Hydroxyethyl methacrylate, 2-Hydroxypropyl methacrylate, Hydroxymethyl methacrylate, N-Vinylpyrrolidone, 2-Vinyl pyridine, 4-Vinyl pyridine, and N-Vinyl-2-methylimidazole.

33. The method of claim 18, wherein the one or more polymerizable monomers comprise Dimethylaminopropyl acrylamide (DMPA).

34. The method of claim 18, wherein the one or more polymerizable monomers are selected from compounds of the following formula:

$$H_2C=C(R^1)-C(O)-X-R^2-N(R^3)_2,$$

wherein $R^1$ is hydrogen, methyl or ethyl group; $R^2$ is a $C_1$-$C_6$-alkyl or aryl group; $R^3$ is a methyl or ethyl group; and X is NH or O.

* * * * *